United States Patent
Chandavarkar et al.

(10) Patent No.: US 8,198,316 B2
(45) Date of Patent: Jun. 12, 2012

(54) PROCESS FOR THE PREPARATION OF 5,6-DIHYDRO-4H-4(S)-ETHYLAMINO-6(S)-METHYLTHIENO[2,3-B]THIOPYRAN-2-SULFONAMIDE-7,7-DIOXIDE AND ITS SALT

(75) Inventors: Anand Mohan Chandavarkar, Maharashtra (IN); Rajaram Uday Bapat, Maharashtra (IN); Anand Atul Bade, Maharashtra (IN); Anand Pandurang Chavan, Maharashtra (IN)

(73) Assignee: FDC Ltd (IN)

( * ) Notice: Subject to any disclaimer, the term of this patent is extended or adjusted under 35 U.S.C. 154(b) by 911 days.

(21) Appl. No.: 11/571,825

(22) PCT Filed: Jul. 6, 2005

(86) PCT No.: PCT/IN2005/000232
§ 371 (c)(1),
(2), (4) Date: Oct. 14, 2008

(87) PCT Pub. No.: WO2006/038222
PCT Pub. Date: Apr. 13, 2006

(65) Prior Publication Data
US 2009/0264662 A1    Oct. 22, 2009

(30) Foreign Application Priority Data
Jul. 9, 2004   (IN) .......................... 741/MUM/2004

(51) Int. Cl.
*A61K 31/38* (2006.01)
*C07D 335/06* (2006.01)

(52) U.S. Cl. .................. 514/432; 514/232.5; 514/233.8; 549/23; 549/66

(58) Field of Classification Search .................. None
See application file for complete search history.

(56) References Cited

U.S. PATENT DOCUMENTS

| | | | |
|---|---|---|---|
| 4,677,115 A | 6/1987 | Baldwin et al. | |
| 4,797,413 A * | 1/1989 | Baldwin et al. | 514/432 |
| 4,968,814 A | 11/1990 | Blacklock et al. | |
| 5,011,942 A | 4/1991 | Blacklock et al. | |
| 5,157,129 A | 10/1992 | Blacklock et al. | |
| 5,441,722 A | 8/1995 | Eng et al. | |
| 5,574,176 A | 11/1996 | Mathre et al. | |
| 5,688,968 A | 11/1997 | Blacklock et al. | |
| 5,760,249 A | 6/1998 | Mathre et al. | |
| 7,030,250 B2 * | 4/2006 | Losada et al. | 549/23 |
| 2003/0220509 A1 * | 11/2003 | Losada et al. | 549/23 |

OTHER PUBLICATIONS

Mathre, David J., et al., "A Practical Process for the Preparation of Tetrayhdro-1-methyl1-3,3-diphenyl-1H,3H-pyrrolo[1,2-c]-[1,3,2]oxazaborole-Borane. A Highly Enantioselective Stoichiometric and Catalytic Reducing Agent", J. Org. Chem. 1993, 58, 2880-2888.

Jones, Todd K., et al., "An Asymmetric Synthesis of MK-0417. Observations on Oxazaborolidine-Catalyzed Reductions", J. Org. Chem. 1991, 56, 763-769.

Blacklock, Thomas, J., et al., "An Enantioselective Synthesis of the Topically-Active Carbonic Anhydrase Inhibitor MK-0507: 5,6-Dihydro-(S)-4-Iethylamino)-(S)-6-methyl-4H-thieno[2,3-b]thiopyran-2-sulfonamide 7,7-Dioxide Hydrocholoride", J. Org. Chem. 1993, 58, 1672-1679.

International Search Report from corresponding application No. PCT/IN2005/000232.

Thomas, Scott M., et al., "In-Process Tests for Synthesis of Dorzolamide Hydrochloride", AT-PROCESSsm, The Journal of Process of Analytical Chemistry, XP002903039, 1997, vol. 2, No. 5-6, pp. 432-439.

Enatiomer Excess from IUPAC's Gold Book, http://goldbook/ipuac.org/E02070.html, 1997, 2nd Edition.

* cited by examiner

*Primary Examiner* — Yate K Cutliff
(74) *Attorney, Agent, or Firm* — Lowe Hauptman Ham & Berner, LLP

(57) ABSTRACT

The present invention relates to resolution of (cis,trans)5,6-dihydro-4H-4-ethylamino-6-methylthieno[2,3-b]thiopyran-2-sulfonamide-7,7-dioxide using dibenzoyl-L-tartaric acid monohydrate or di-p-toluoyl-L-tarrtaric acid monohydrate as a chiral resolving agent in presence of methanol to obtain hemitartarate salt, purifying it to obtain hemitartarate salt of 5,6-dihydro-4H-4(S)-ethylamino-6(S)methylthieno[2,3-b]thiopyran-2-sulfonamide-7,7-dioxide with de of >99%, Chemical purity >99.5% with cis isomer content of <0.1% and further converting into its pharmaceutically acceptable salts, preferably hydrochloride salt.

15 Claims, No Drawings

PROCESS FOR THE PREPARATION OF 5,6-DIHYDRO-4H-4(S)-ETHYLAMINO-6(S)-METHYLTHIENO[2,3-B]THIOPYRAN-2-SULFONAMIDE-7,7-DIOXIDE AND ITS SALT

RELATED APPLICATIONS

The present application is a National Phase entry of International Application No. PCT/IN2005/000232, filed Jul. 6, 2005, which claims priority from, Indian Application Number 741/MUM/2004, filed Jul. 9, 2004, the disclosures of which are hereby incorporated by reference herein in their entirety.

TECHNICAL FIELD

This invention relates to an improved process for the preparation of 5,6-dihydro-4H-4(S)-ethylamino-6(S)-methylthieno[2,3-b]thiopyran-2-sulfonamide-7,7-dioxide with a high chemical and optical purity comprising resolution of (cis, trans)5,6-dihydro-4H-4-ethylamino-6-methylthieno[2,3-b]thiopyran-2-sulfonamide-7,7-dioxide using di-O-benzoyl-L-tartaric acid monohydrate or di-O-toluoyl-L-tartaric acid monohydrate as chiral resolving agent.

BACKGROUND AND PRIOR ART OF THE INVENTION

Increase in intraocular pressure is one of the causes of eye disease known as glaucoma. If not treated in time high intraocular pressure may result in loss of vision. Among the latest therapeutic agents used in the treatment of glaucoma are topically active carbonic anhydrase inhibitors. They target the desired ophthalmic tissue hence have very less side effects as compared to their systemic counterparts, which inhibit carbonic anhydrase throughout the entire body.

5,6-dihydro-4H-4(S)-ethylamino-6-(S)-methylthieno[2,3-b]thiopyran-2-sulfonamide-7,7-dioxide is used in the treatment of elevated intraocular pressure, especially when accompanied by pathological damage such as the disease known as glaucoma.

Among the leading topically active carbonic anhydrase inhibitors is a hydrochloride salt of 5,6-dihydro-4H-4(S)-ethylamino-6(S)-methylthieno[2,3-b]thiopyran-2-sulfonamide-7,7-dioxide generically known as Dorzolamide hydrochloride (I) originally described in U.S. Pat. No. 4,797,413.

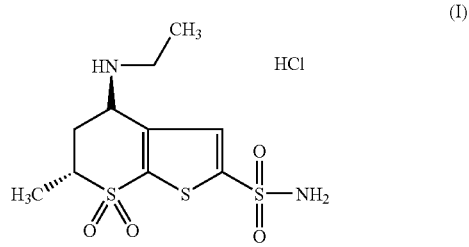

(I)

U.S. Pat. Nos. 5,688,968, 5,441,722 and 5,157,129 describe improved processes for preparing (I).

Dorzolamide HCI (I) contains two chiral centers and can exist in four diastereoisomeric forms.

The U.S. Pat. No. 4,797, 413 describes a process to prepare racemic version of (I) and a process for resolution of trans-5,6-dihydro-4H-4-ethylamino-6-methylthienol[2,3-b]thiopyran-2-sufonamide-7,7-dioxide.

The prior art resolution process, wherein trans 5,6-dihydro-4H-4-ethylamino-6-methylthieno[2,3-b]thiopyran-2-sulfonamide-7,7-dioxide is resolved employing two chiral resolving agents viz. di-p-toluoyl-D-tartaric acid monohydrate and di-p-toluoyl-L-Tartaric acid monohydrate in a solvent media n-propanol. The required (S,S) diastereoisomer is isolated from mother liquor after separating unwanted diastereoisomer in a two stage resolution process The overall process for resolution described in the prior art is tedious and not favourable for scale up. The use of unnatural tartaric acid derivative which is expensive adds to the cost of the process. Further there is no mention about the chemical purity of compound (I) obtained.

The surprising result of the present invention is achieved by obtaining the required diasterioisomer 5-6,dihydro-4H-4(S)-ethylamino-6(S)-methyl thieno[2,3-b]thiopyran-2-sulphonamide-7,7-dioxide having high optical and chemical purity only by using either dibenzoyl-L-tartaric acid or di-p-toluoyl-L-tartaric acid as a chiral resolving agent in presence of an organic solvent preferably methanol as a solvent, starting from (cis,trans)5-6,dihydro-4H-4-ethylamino-6methyl thieno[2,3-b]thiopyran-2-sulphonamide-7,7-dioxide in one stage resolution process. So far 5-6,dihydro-4H-4(S)-ethylamino-6(S)-methyl thieno[2,3-b]thiopyran-2-sulphonamide-7,7-dioxide has not been obtained by resolving (cis, trans) 5-6,dihydro-4H-4-ethylamino-6methyl thieno[2,3-b]thiopyran-2-sulphonamide-7,7-dioxide using single chiral resolving agent. The process of the present invention also enables selective separation of hemihydrate salt of (s,s)-trans isomer of high purity as an intermediate for obtaining the final product (s,s) dorzolamide and its pharmaceutically acceptable salt.

Thus, process of the present invention used for resolution is novel and inventive over the prior art process.

OBJECTS OF THE INVENTION

An object of the present invention is to prepare 5,6-dihydro-4H-4(S)-ethylamino-6(S)-methylthieno[2,3-b]thiopyran-2-sulfonamide-7,7-dioxide by resolution of (cis, trans)5,6-dihydro-4H-4ethylamino-6-methylthieno[2,3-b]thiopyran-2-sulfonamide-7,7-dioxide using dibenzoyl-L-tartaric acid or di-p-toluoyl-L-tarrtaric acid as a chiral resolving agent and an organic solvent preferably methyl alcohol as solvent.

Another object of the present invention is to provide a compound 5,6-dihydro-4H-4(S)-ethylamino-6(S)-methylthieno[2,3-b]thiopyran-2-sulfonamide-7,7-dioxide having high chemical and optical purity.

Still another object of the present invention is to provide 5,6-dihydro-4H-4(S)-ethylamino-6(S)methylthieno[2,3-b]thiopyran-2-sulfonamide-7,7-dioxide having 5,6-dihydro-4H-4(R)-ethylamino-6(R)methylthieno[2,3-b]thiopyran-2-sulfonamide-7,7-dioxide isomer content of less than 0.5% w/w.

Yet another object of the present invention is to provide 5,6-dihydro-4H-4(S)-ethylamino-6(S)methylthieno[2,3-b]thiopyran-2-sulfonamide-7,7-dioxide thus obtained having cis isomer content of less than 0.1% w/w, total impurities at a level of less than 0.3% w/w and purity of more than 99.5% by HPLC.

Still yet another object of the present invention is to provide a process for resolution which is simple, economical starting from (cis,trans)5,6-dihydro-4H-4-ethylamino-6-methylthieno[2,3-b]thiopyran-2-sulfonamide-7,7-dioxide.

SUMMARY OF THE INVENTION

This invention relates to an improved process for the preparation of 5,6-dihydro-4H-4(S)-ethylamino-6(S)-methylthieno[2,3-b]thiopyran-2-sulfonamide-7,7-dioxide with a high chemical and optical purity comprising resolution of (cis, trans)5,6-dihydro-4H-4-ethylamino-6-methylthieno[2,3-b]thiopyran-2-sulfonamide-7,7-dioxide by treating with either di-O-benzoyl-L-tartaric acid monohydrate or di-O-toluoyl-L-tartaric acid monohydrate chiral resolving agents in an organic solvent, preferably methanol to obtain an intermediate hemitartarate salt, which on further purification yielded (s,s) Dorzolamide free base, converting to its hydrochloride by treating with isopropanol-hydrochloride followed by crystallization from isopropanol.

DETAILED DESCRIPTION OF THE PRESENT INVENTION

In accordance with the object, the present invention provides an improved process for the preparation of 5,6-dihydro-4H-4(S)-ethylamino-6(S)methylthieno[2,3-b]thiopyran-2-sulfonamide-7,7-dioxide hydrochloride comprising steps of:
a) contacting(cis,trans)5,6-dihydro-4H-4-ethylamino-6-methylthieno[2,3-b]thiopyran-2-sulfonamide-7,7-dioxide with di-O-substituted-L-tartaric acid in an organic solvent,
b) obtaining intermediate hemitartarate salt of formula(IV)

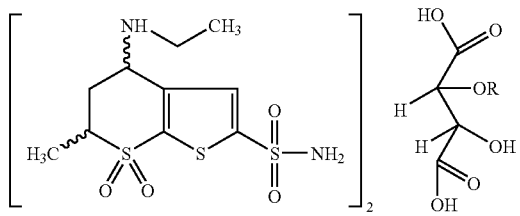

c) Refluxing hemitartarate salt of step b) With methanol to obtain purified hemitartarate salt treating the purified hemitartarate salt of step (c) with ethylacetate and aqueous alkali bicarbonate solution, separating ethylacetate and aqueous layer,
d) Extracting the aqueous layer of step (d) with ethylacetate, separating the ethylacetate layer,
e) Combining ethylacetate layers of step (c) and (d), washing with water, collecting water washed ethylacetate layer to obtain 5,6-dihydro-4H-4(S)-ethylamino-6(S) methylthieno [2,3-b]thiopyran-2-sulfonamide-7,7-dioxide,
f) adjusting the pH between 1.0 to 2.0 of ethylacetate layer with isopropanol-hydrochloric acid solution, and
g) separating the precipitated solid and crystallizing the solid from isopropanol.

An embodiment of the process uses an organic solvent methanol in step a).

Another embodiment of the process wherein chiral resolving agent di-O-substituted L-tartaric acid used is selected from a group consisting of di-O-benzoyl-L-tartaric acid monohydrate and di-O-p-toluoyl-L-tartaric acid monohydrate.

Still another embodiment of the process wherein di-O-substituted-L-tartaric acid used is preferably di-O-benzoyl-L-tartaric acid monohydrate.

Yet another embodiment of the process uses aqueous alkali carbonate solution selected from the group consisting of aqueous potassium carbonate and aqueous sodium carbonate solution, preferably aqueous sodium carbonate solution The novel resolution process of this invention used to resolve (cis, trans)5,6-dihydro-4H-4-ethylamino-6-methylthieno[2,3-b]thiopyran-2-sulfonamide-7,7-dioxide into required 5,6-dihydro-4H-4(S)-ethylamino-6(S)-methylthieno[2,3-b]thiopyran-2-sulfonamide-7,7-dioxide as depicted below:

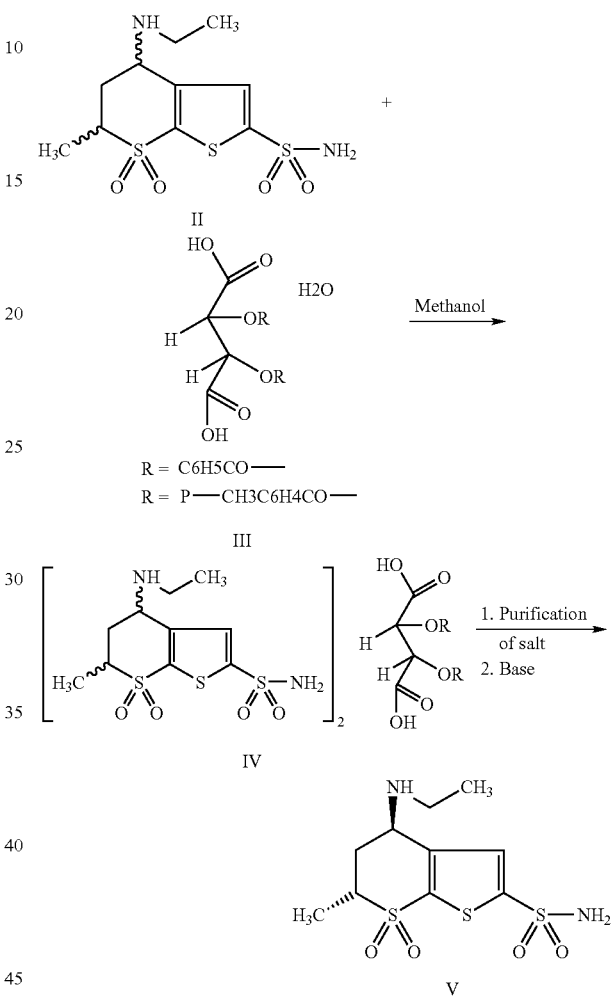

Several solvents namely methanol, ethanol, isopropanol, t-butanol, water or its mixture were used for resolution. The best possible resolution is achieved using a combination of chiral resolving agent di-O-benzoyl-L-tartaric acid and methanol as the solvent.

A resolution process of this invention comprises reacting (cis,trans)5,6-dihydro-4H-4-ethylamino-6-methylthieno[2,3-b]thiopyran-2-sulfonamide-7,7-dioxide with dibenzoyl-L tartaric acid monohydrate or di-p-toluoyl-L tartaric acid monohydrate in methanol as solvent. The resulting solution is filtered and stirred to obtain hemitartarate salt of 5,6-dihydro-4H-4(S)-ethylamino-6(S)-methylthieno[2,3-b]thiopyran-2-sulfonamide-7,7-dioxide with de (diastereomer excess) of >95%.The salt on purification yields pure hemitartarate salt having de of >99% and Chemical purity >99.5% with cis isomer content of <0.1%. The purification of hemitartarate salt is advantageously carried out in a soxhlet type apparatus.

The 5,6-dihydro-4H-4(S)-ethylamino-6(S)methylthieno [2,3-b]thiopyran-2-sulfonamide-7,7-dioxide obtained from purified hemitartarate is further converted into its pharmaceutically acceptable salts, preferably hydrochloride salt.

The features of the present invention will become more apparent from the following description of the inventive concept and the description of the preferred embodiments and appended claims.

EXAMPLES

Example 1

A solution of Dibenzoyl-L-tartaric acid (16.30 gms) in of methanol (35 ml) & (cis,trans)5,6-dihydro-4H-4-ethylamino-6-methylthieno[2,3-b]thiopyran-2-sulfonamide-7,7-dioxide (14 gms) in methanol (125 ml) were stirred at 25° C. to 30° C. till a clear solution was obtained. The clear solution was further stirred for 24 hours, separated solid was filtered off, dried and recrystallized from methanol (~100 ml). The recrystallized material was treated twice with methanol (~150 ml) in a soxhlet apparatus. The purified material so obtained was further treated with a mixture of ethyl acetate (35 ml) and 2% sodium carbonate solution(35 ml). The layers were separated, the aqueous layer was again extracted with ethyl acetate(20 ml) and the combined organic extracts were washed with water (20 ml). The pH of the washed organic extract was adjusted between 1.0 to 2.0 with IPA/HCl, separated the solid by filtration to obtain ethylacetate filtrate and solid dried to yield 2.4 gms of (s,s) dorzolamide hydrochloride salt The hydrochloride salt obtained (2.4 gms) was recrystallized from IPA(15 ml) to give 2.4 gms of 5,6-dihydro-4H-4(S)-ethylamino-6(S)-methylthieno[2,3-b]-thiopyran-2-sulfonamide-7,7-dioxide hydrochloride. The ethylacetate filtrate was kept aside for recovery of (cis,trans)5,6-dihydro-4H-4-ethylamino-6-methylthieno[2,3-b]thiopyran-2-sulfonamide-7,7-dioxide.

Example 2

Recovery of the (cis,trans)5,6-dihydro-4H-4-ethylamino-methylthieno[2,3-b]thiopyran-2-sulfonamide-7,7-dioxide from the Ethyl Acetate filtrate. The ethylacetate filtrate of example 1 was washed with 2% sodium carbonate solution till pH of around 8 was attained. The layers were separated and aqueous layer extracted with ethyl acetate. The ethyl acetate extracts were combined and washed with water. The washed ethyl acetate layer was concentrated to around 15% of original volume to yield 4.6 gms. of (cis,trans) 5,6-dihydro-4H-4-ethylamino-6-methylthieno[2,3-b]thiopyran-2-sulfonamide-7,7-dioxide, which was further resolved using the same process of example 1 to obtain (s,s) dorzolamide and its salt.

MAIN Advantages of the Invention

1) Process uses only naturally occurring chiral resolving agent.
2) Process is simple and economical.

REFERENCES a. U.S. Pat. No. 5,011,942
b. U.S. Pat. No. 4,797,413
c. U.S. Pat. No. 5,157,129
d. U.S. Pat. No. 5,441,722
e. U.S. Pat. No. 5,574,176
f. U.S. Pat. No. 4,968,814
g. U.S. Pat. No. 5,760,249
h. U.S. Pat. No. 4,677,115
i. U.S. Pat. No. 5,688,968
j. JOC 1993, 58, 1672-1679
k. JOC 1991, 56, 763-769
l. JOC 1993, 58, 2880-2888.

We claim:

1. A process for the preparation of 5,6-dihydro-4H-4(S)-ethylamino-6(S) methylthieno [2,3-b]thiopyran-2-sulfonamide-7,7-dioxide hydrochloride comprising:
   a. contacting (cis,trans)5,6-dihydro-4H-4-ethylamino-6-methylthieno [2,3-b]thiopyran-2-sulfonamide-7,7-dioxide with a form of di-O-substituted-L-tartaric acid in an organic solvent to obtain intermediate hemitartarate salt of formula IV,

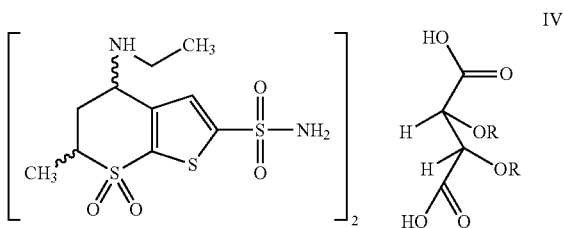

wherein R is $C_6H_5CO—$ or $p—CH_3C_6H_4CO—$, and wherein the form of di-O-substituted L-tartaric acid is selected from a di-O-benzoyl-L-tartaric acid monohydrate and a di-O-p-toluoyl-L-tartaric acid monohydrate,
   b. refluxing the hemitartarate salt with methanol to obtain pure hemitartarate salt,
   c. treating the purified hemitartarate salt with ethylacetate and an aqueous alkali carbonate solution, separating ethylacetate and aqueous layer,
   d. extracting the aqueous layer with ethylacetate, separating the ethylacetate layer,
   e. combining ethylacetate layers of (c) and (d), washing with water, collecting water washed ethylacetate layer to obtain 5,6-dihydro-4H-4(S)-ethylamino-6(S)methylthieno [2,3-b]thiopyran-2-sulfonamide-7,7-dioxide,
   f. adjusting pH of ethylacetate layer between 1.0 and 2.0 with isopropanol-hydrochloric acid solution, and
   g. separating the precipitated solid and crystallizing from isopropanol.

2. A process of claim 1, wherein the organic solvent used is methanol.

3. A process for the preparation of 5,6-dihydro-4H-4(S)-ethylamino-6(S)methylthieno [2,3-b]thiopyran-2-sulfonamide-7,7-dioxide hydrochloride comprising:
   a. contacting (cis,trans)5,6-dihydro-4H-4-ethylamino-6-methylthieno [2,3-b]thiopyran-2-sulfonamide-7,7-dioxide with a form of di-O-substituted-L-tartaric acid in an organic solvent to obtain intermediate hemitartarate salt of formula IV,

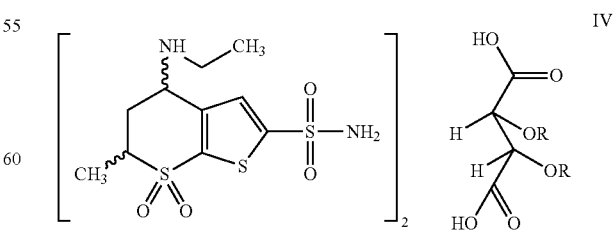

wherein R is $C_6H_5CO—$, wherein the form of di-O-substituted L-tartaric acid is a di-O-benzoyl-L-tartaric acid monohydrate, b. refluxing the hemitartarate salt with methanol to obtain pure hemitartarate salt, c. treating the purified hemitartarate salt with ethylacetate and an aqueous alkali carbonate solution, separating ethylacetate and aqueous layer, d. extracting the aqueous layer with ethylacetate, separating the ethylacetate layer, e. combining ethylacetate layers of (c) and (d), washing with water, collecting water washed ethylacetate layer to obtain 5,6-dihydro-4H-4(S)-ethylamino-6(S)methylthieno[2,3-b]thiopyran-2-sulfonamide -7,7-dioxide, f. adjusting pH of ethylacetate layer between 1.0 and 2.0 with isopropanol-hydrochloric acid solution, and g. separating the precipitated solid and crystallizing from isopropanol.

4. A process of claim 1, wherein the aqueous alkali carbonate solution is aqueous potassium carbonate solution or aqueous sodium carbonate solution.

5. A process of claim 1 wherein the aqueous alkali carbonate solution is aqueous sodium carbonate solution.

6. A process of claim 3, wherein the organic solvent is methanol.

7. A process of claim 3, wherein the aqueous alkali carbonate solution is aqueous potassium carbonate solution or aqueous sodium carbonate solution.

8. A process of claim 3, wherein the aqueous alkali carbonate solution is aqueous sodium carbonate solution.

9. A process of claim 3, wherein di-O-benzoyl-L-tartaric acid monohydrate is added to the organic solvent of step a.

10. A process of claim 1, wherein di-O-benzoyl-L-tartaric acid monohydrate or di-O-p-toluoyl-L-tartaric acid monohydrate is added to the organic solvent of step a.

11. A process for the preparation of 5,6-dihydro-4H-4(S)-ethylamino-6(S)methylthieno [2,3-b]thiopyran-2-sulfonamide-7,7-dioxide hydrochloride comprising:

a. contacting (cis,trans)5,6-dihydro-4H-4-ethylamino-6-methylthieno[2,3-b]thiopyran-2-sulfonamide-7,7-dioxide with a form of di-O-substituted-L-tartaric acid in an organic solvent to obtain intermediate hemitartarate salt of formula IV,

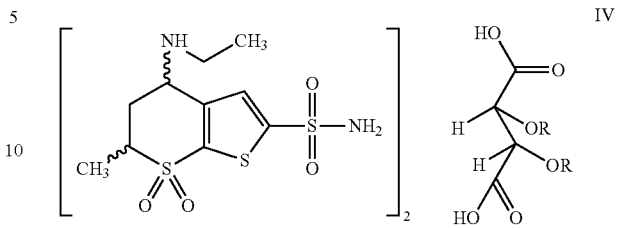

wherein R is p-$CH_3C_6H_4CO$—, and wherein the form of di-O-substituted L-tartaric acid is selected from a di-O-p-toluoyl-L-tartaric acid monohydrate, b. refluxing the hemitartarate salt with methanol to obtain pure hemitartarate salt, c. treating the purified hemitartarate salt with ethylacetate and an aqueous alkali carbonate solution, separating ethylacetate and aqueous layer, d. extracting the aqueous layer with ethylacetate, separating the ethylacetate layer, e. combining ethylacetate layers of (c) and (d), washing with water, collecting water washed ethylacetate layer to obtain 5,6-dihydro-4H-4(S)-ethylamino-6(S)methylthieno [2,3-b]thiopyran-2-sulfonamide-7,7-dioxide, f. adjusting pH of ethylacetate layer between 1.0 and 2.0 with isopropanol-hydrochloric acid solution, and g. separating the precipitated solid and crystallizing from isopropanol.

12. A process of claim 11, wherein the organic solvent is methanol.

13. A process of claim 11, wherein the aqueous alkali carbonate solution is aqueous potassium carbonate solution or aqueous sodium carbonate solution.

14. A process of claim 11, wherein the aqueous alkali carbonate solution is aqueous sodium carbonate solution.

15. A process of claim 11, wherein di-O-p-toluoyl-L-tartaric acid monohydrate is added to the organic solvent of step a.

* * * * *